United States Patent
Heo et al.

(10) Patent No.: US 12,412,916 B2
(45) Date of Patent: Sep. 9, 2025

(54) FUEL CELL WITH POLYMER ELECTROLYTE MEMBRANE

(71) Applicants: HYUNDAI MOTOR COMPANY, Seoul (KR); Kia Corporation, Seoul (KR); INDUSTRY-ACADEMIC COOPERATION FOUNDATION GYEONGSANG NATIONAL UNIVERSITY, Jinju-si (KR)

(72) Inventors: Pil Won Heo, Yongin-si (KR); Jong Myung Lee, Yongin-si (KR); Sung Chul Lee, Yongin-si (KR); Ki Hyun Kim, Yongin-si (KR); Byeong Seon Kim, Jinju-si (KR); Han Sol Ko, Changwon-si (KR); Mi Jeong Kim, Gimhae-si (KR); Yu Gyeong Jeong, Changwon-si (KR); Sean Soo Hwang, Gimhae-si (KR)

(73) Assignees: HYUNDAI MOTOR COMPANY, Seoul (KR); KIA CORPORATION, Seoul (KR); INDUSTRY-ACADEMIC COOPERATION FOUNDATION GYEONGSANG NATIONAL UNIVERSITY, Jinju-si (KR)

( * ) Notice: Subject to any disclaimer, the term of this patent is extended or adjusted under 35 U.S.C. 154(b) by 303 days.

(21) Appl. No.: 17/979,270

(22) Filed: Nov. 2, 2022

(65) Prior Publication Data
US 2023/0317998 A1    Oct. 5, 2023

(30) Foreign Application Priority Data
Apr. 4, 2022    (KR) .......................... 10-2022-0041854

(51) Int. Cl.
*H01M 8/1032*    (2016.01)
*C07C 309/10*    (2006.01)
(Continued)

(52) U.S. Cl.
CPC ......... *H01M 8/1032* (2013.01); *C07C 309/10* (2013.01); *C08K 5/41* (2013.01);
(Continued)

(58) Field of Classification Search
CPC ............. H01M 8/1032; H01M 8/1004; H01M 8/1027; H01M 8/1039; H01M 8/1067;
(Continued)

(56) References Cited

U.S. PATENT DOCUMENTS 7,868,124 B2    1/2011    Balland-Longeau et al.
8,628,885 B2    1/2014    Yamaguchi et al.
(Continued)

FOREIGN PATENT DOCUMENTS

CN    1675279 A    9/2005
CN    102077393 A    5/2011
(Continued)

OTHER PUBLICATIONS

Extended European search report issued on Aug. 28, 2023, in counterpart European Patent Application No. 22202071.1 (6 pages).
(Continued)

*Primary Examiner* — Daniel S Gatewood
(74) *Attorney, Agent, or Firm* — MORGAN, LEWIS & BOCKIUS LLP

(57) ABSTRACT

A compound is represented by Formula 1 below:

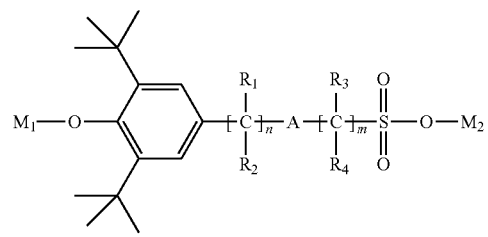

wherein $R_1$ to $R_4$ are each independently a hydrogen atom, an alkyl group having 1 to 6 carbon atoms, a fluoro-substituted alkyl group having 1 to 6 carbon atoms, or a fluorine atom, wherein at least one among $R_1$ to $R_4$ is a fluorine atom, A is a divalent linking group, $M_1$ and $M_2$ are
(Continued)

each independently potassium or sodium, and n and m are each independently an integer of 1 to 10.

15 Claims, 8 Drawing Sheets

(51) Int. Cl.
  C08K 5/41     (2006.01)
  H01M 8/10     (2016.01)
  H01M 8/1004   (2016.01)
  H01M 8/1027   (2016.01)
  H01M 8/1039   (2016.01)
  H01M 8/1067   (2016.01)

(52) U.S. Cl.
  CPC ....... *H01M 8/1004* (2013.01); *H01M 8/1027* (2013.01); *H01M 8/1039* (2013.01); *H01M 8/1067* (2013.01); *H01M 2008/1095* (2013.01)

(58) Field of Classification Search
  CPC ..... H01M 2008/1095; H01M 8/04089; H01M 8/1018; H01M 8/1041; C07C 309/10; C08K 5/41; C08K 5/42; C08K 5/0091; Y02E 60/50; C08J 5/2281; C08J 2327/18; C07F 1/04; C07F 1/06; C08G 61/02
  See application file for complete search history.

(56) References Cited

U.S. PATENT DOCUMENTS

| | | |
|---|---|---|
| 9,136,551 B2 | 9/2015 | Kwon et al. |
| 2006/0106190 A1 | 5/2006 | Balland-Longeau et al. |
| 2011/0250509 A1 | 10/2011 | Yamaguchi et al. |
| 2014/0065512 A1* | 3/2014 | Kwon ................ H01M 8/1048 562/42 |
| 2015/0328630 A1* | 11/2015 | Yoo ...................... C07C 309/10 562/42 |
| 2017/0174914 A1 | 6/2017 | Matsumura et al. |

FOREIGN PATENT DOCUMENTS

| | | |
|---|---|---|
| CN | 103517912 A | 1/2014 |
| EP | 2 987 795 A2 | 2/2016 |
| JP | 2003-292608 A | 10/2003 |
| JP | 2021-168260 A | 10/2021 |
| KR | 10-2010-0006809 A | 1/2010 |
| WO | WO 2010/005267 A2 | 1/2010 |

OTHER PUBLICATIONS

Office Action issued in corresponding Chinese Patent Application No. 2022113755536 dated Apr. 16, 2025, with English translation.

* cited by examiner

FUEL CELL WITH POLYMER ELECTROLYTE MEMBRANE

CROSS-REFERENCE TO RELATED APPLICATIONS

This application claims the benefit under 35 USC 119 (a) of Korean Patent Application No. 10-2022-0041854 filed on Apr. 4, 2022, in the Korean Intellectual Property Office, the entire disclosure of which is incorporated herein by reference for all purposes.

BACKGROUND

Field

The following description relates a fuel cell with polymer electrolyte.

Description of the Related Art

Recently, the depletion of existing fossil energy resources such as oil and coal is predicted, and various limitations such as thermal power generation that causes a large amount of greenhouse gases and environmental pollution problems using the fossil energy resources, or nuclear power generation that has problems of stability of the facility itself or waste treatment have been revealed, and interests in alternative energy sources which are more eco-friendly and have high efficiency are being increased. As one of such alternative energy sources, a fuel cell is particularly attracting attention due to advantages such as high efficiency, no emission of pollutants such as NOx and SOx, and abundant fuel to be used.

Among the fuel cells, polymer electrolyte fuel cells have been developed in various ways since proposed in the 1950s for the purpose of supplying energy to a spacecraft, and include a proton exchange membrane fuel cell (PEMFC) using a hydrogen gas as fuel and a direct methanol fuel cell (DMFC) using liquid methanol as direct fuel supplied to a positive electrode. The supplied fuels, hydrogen and methanol, are almost permanent and produce only water as by-products through electrochemical reactions.

The fuel cell includes a membrane electrode assembly including an anode, a cathode and a hydrogen ion conductive polymer electrolyte membrane located therebetween, and hydrogen or methanol supplied to the anode (oxidation electrode, positive electrode) forms hydrogen ions through a catalytic reaction, the formed hydrogen ions move to the cathode (reduction electrode, negative electrode) through the hydrogen ion conductive polymer electrolyte membrane, and meet electrons, which are moved through an external circuit, and air or oxygen, which is supplied to the cathode, so that water, electric energy, and heat are generated through the reduction reaction.

Numerous types of sulfonated polymers and polymer compositions have been tested as a hydrogen ion conductive polymer electrolyte membrane. However, the sulfonated polymer has a hydrogen ion transfer function in the hydrated state, and accordingly, there are problems in that when the fuel cell is operated at a high temperature of 90° C. or higher, the moisture in the polymer electrolyte membrane decreases and the proton conductivity decreases rapidly due to decomposition of the sulfonic acid group at a high temperature. Various methods have been studied to solve these problems, and typically, there are a method for solving the reduction of proton conductivity at a high temperature of 100° C. or higher by introducing an inorganic oxide such as $TiO_2$, $SiO_2$, $Al_2O_3$, $ZrO_2$, tetraethoxysilane (TEOS), montmorillonite, or mordenite to a perfluorinated sulfonated ionomer such as Nafion to improve the moisture carrying capacity at a high temperature, and a method for offsetting the reduction of the moisture carrying capacity at a high temperature and the consequent reduction of proton conductivity by introducing heteropolyacid (HPA) such as zirconium phosphoric acid (ZrP), phosphotungstic acid, silicotungstic acid, phospho molybdic acid, and silico molybdic acid having proton conductivity. However, the introduction of the inorganic oxide has a limitation in securing balanced physical properties such as mechanical properties and chemical durability because the inorganic oxide is not uniformly dispersed, and there is a limitation in that the mechanical properties are deteriorated, or basic performances of the polymer electrolyte membrane, such as proton conductivity, thermal stability, and hydration stability, are deteriorated.

Accordingly, there is a need to develop an additive for a polymer electrolyte membrane that can harmoniously improve performances such as mechanical properties, chemical durability, thermal stability, and proton conductivity of the polymer electrolyte membrane.

Prior Art Document

PATENT DOCUMENTS (Patent Document 1) KR 10-2010-0006809 A

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a compound is represented by Formula 1 below:

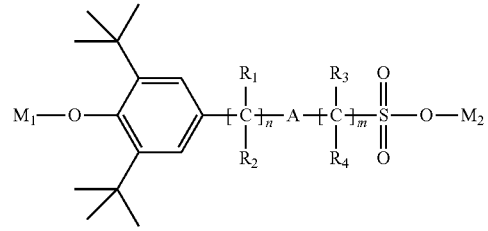

wherein $R_1$ to $R_4$ are each independently a hydrogen atom, an alkyl group having 1 to 6 carbon atoms, a fluoro-substituted alkyl group having 1 to 6 carbon atoms, or a fluorine atom, wherein at least one among $R_1$ to $R_4$ is a fluorine atom, A is a divalent linking group, $M_1$ and $M_2$ are each independently potassium or sodium, and n and m are each independently an integer of 1 to 10.

$R_1$ to $R_4$ may each independently be the hydrogen atom, where at least one among $R_1$ to $R_4$ is the fluorine atom.

The alkyl group may have 1 to 3 carbon atoms, where at least one among $R_1$ to $R_4$ is the fluorine atom.

The fluoro-substituted alkyl group may have 1 to 3 carbon atoms, where at least one among $R_1$ to $R_4$ is the fluorine atom.

$R_1$ to $R_4$ may be the fluorine atom.

In Formula 1, A may be —O— or —S—.

In Formula 1, $M_1$ and $M_2$ may each independently be potassium.

$M_1$ and $M_2$ may be sodium.

$R_1$ to $R_4$ may all be fluorine atoms, A may be —O—, $M_1$ and $M_2$ may be sodium, and n and m may each independently be an integer of 1 to 3.

The compound represented by Formula 1 may be represented by Formula 1-1 below:

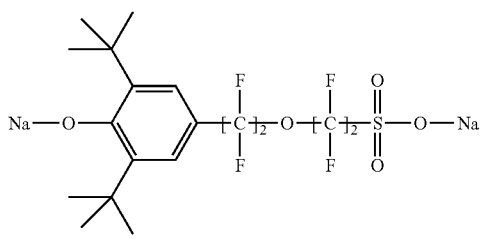

A polymer electrolyte membrane may include the compound disclosed.

The polymer electrolyte membrane may have a proton conductivity of 24 mS/cm to 38 mS/cm under the conditions of 80° C. and 50% relative humidity (RH).

The polymer electrolyte membrane may have a proton conductivity of 92 mS/cm to 120 mS/cm under the conditions of 80° C. and 90% relative humidity (RH).

The polymer electrolyte membrane may include a polymer support and the compound is comprised in an amount of 0.5 wt % to 2.0 wt % based on a weight of the polymer support.

In another general aspect, a membrane electrode assembly includes an anode, a cathode, and the polymer electrolyte membrane disclosed disposed between the anode and the cathode.

In another general aspect, a fuel cell includes a stack including the at least two membrane electrode assemblies disclosed, and a separator disposed between the membrane electrode assemblies, a fuel supplier configured to supply fuel to the stack, and an oxidizer supplier configured to supply an oxidizer to the stack.

Other features and aspects will be apparent from the following detailed description, the drawings, and the claims.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION

Figure 1:
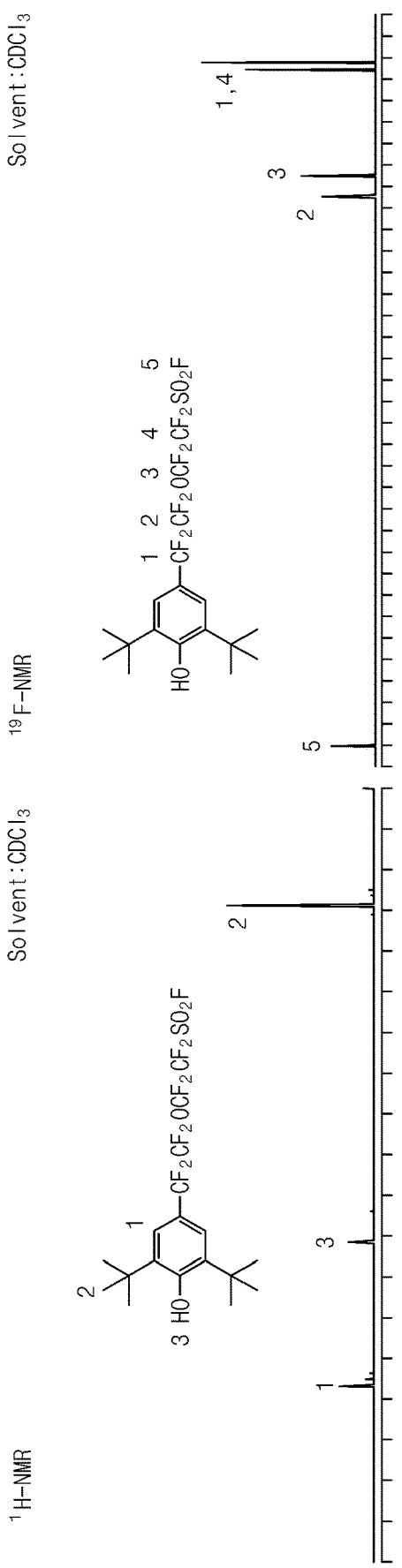
FIG. 1 shows the results of $^1$H NMR and $^{19}$F NMR of a precursor compound prepared in Example 1 according to an embodiment of the present disclosure.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known after understanding of the disclosure of this application may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Spatially relative terms such as "above," "upper," "below," and "lower" may be used herein for ease of description to describe one element's relationship to another element as shown in the figures. Such spatially relative terms are intended to encompass different orientations of the device in use or operation in addition to the orientation depicted in the figures. For example, if the device in the figures is turned over, an element described as being "above"

or "upper" relative to another element will then be "below" or "lower" relative to the other element. Thus, the term "above" encompasses both the above and below orientations depending on the spatial orientation of the device. The device may also be oriented in other ways (for example, rotated 90 degrees or at other orientations), and the spatially relative terms used herein are to be interpreted accordingly.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Due to manufacturing techniques and/or tolerances, variations of the shapes shown in the drawings may occur. Thus, the examples described herein are not limited to the specific shapes shown in the drawings, but include changes in shape that occur during manufacturing.

The features of the examples described herein may be combined in various ways as will be apparent after an understanding of the disclosure of this application. Further, although the examples described herein have a variety of configurations, other configurations are possible as will be apparent after an understanding of the disclosure of this application.

It will be understood that words or terms used in the description and claims of the present disclosure shall not be construed as being limited to having the meaning defined in commonly used dictionaries. It will be further understood that the words or terms should be interpreted as having meanings that are consistent with their meanings in the context of the relevant art and the technical idea of the disclosure, based on the principle that an inventor may properly define the meaning of the words or terms to best explain the disclosure.

DEFINITION OF TERMS

As used herein, the term "antioxidant functional group" refers to a functional group that plays a role in suppressing oxidation by having a property of preventing and suppressing a function of active oxygen under conditions such as light and heat with respect to an oxidizing material, and for example, a functional group that serves as an antioxidant by reacting with oxygen radicals of reactive oxygen species (ROS) instead of a polymer electrolyte membrane in an environment in which the polymer electrolyte membrane is attacked by radicals.

As used herein, the term "ion conductive functional group" refers to a functional group that increases ion conductivity, particularly proton conductivity, and for example, a functional group that does not form an ion bond with an anionic functional group of a polymer electrolyte membrane or suppresses the formation thereof, thereby suppressing a decrease in ion conductivity.

As used herein, the term "membrane electrode assembly (MEA)" refers to an assembly of an electrode (anode and cathode) in which an electrochemical catalyst reaction between fuel and air occurs and a polymer electrolyte membrane in which hydrogen ions are transferred, and refers to a single integral unit in which the electrode (anode and cathode) and the polymer electrolyte membrane are bonded.

It will be further understood that the terms "comprising," "including," and "having" and the derivatives thereof as used herein, though these terms are particularly disclosed or not, are not intended to preclude the presence or addition of optional components, steps, or processes. In order to avoid any uncertainty, all materials and methods claimed by using the term "comprising" may include optional additional additives, auxiliaries, or compounds, unless otherwise described. In contrast, the term "consisting essentially of" excludes unnecessary ones for operation and precludes optional other components, steps or processes from the scope of optional continuous description. The term "consisting of" precludes optional components, steps or processes, which are not particularly described or listed.

[Measurement Methods and Conditions]

In the present specification, the "proton conductivity" is measured by cutting a polymer electrolyte membrane into a specimen having a size of 0.5 cm×3 cm, engaging the specimen with a four-probe cell, maintaining a temperature/humidity equilibrium for 2 hours under conditions of 80° C. and 70% relative humidity (RH) before measurement, and measuring the proton conductivity by dropping the humidity from 70% RH to 20% RH, and then measuring the proton conductivity by increasing the humidity from 20% RH to 100% RH by using BekkTech BT-552MX equipment.

Novel Compound

The present disclosure provides a compound with a novel structure which is applied as an additive for a polymer electrolyte membrane, thereby improving the chemical durability, thermal stability, and mechanical stability of the polymer electrolyte membrane and simultaneously improving performance such as proton conductivity.

The compound according to an embodiment of the present disclosure is represented by Formula 1 below:

[Formula 1]

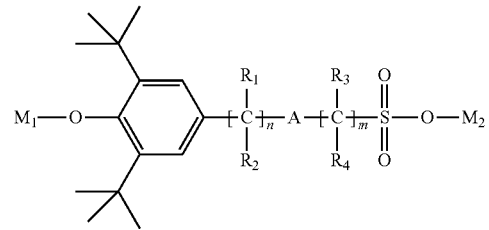

In Formula 1 above, $R_1$ to $R_4$ are each independently a hydrogen atom, an alkyl group having 1 to 6 carbon atoms, a fluoro-substituted alkyl group having 1 to 6 carbon atoms, or a fluorine atom, wherein at least one among $R_1$ to $R_4$ is a fluorine atom, A is a divalent linking group, $M_1$ and $M_2$ are each independently potassium or sodium, and n and m are each independently an integer of 1 to 10.

The compound represented by Formula 1 above according to an embodiment of the present disclosure includes both an antioxidant functional group and an ion conductive functional group in the molecule, and thus is applied as an organic additive for the polymer electrolyte membrane, thereby preventing the oxidation of the polymer electrolyte membrane and improving ion conductivity.

Specifically, as the polymer electrolyte membrane, for example, a sulfonated polymer electrolyte membrane is widely used, which is prepared by preparing a membrane from a polymer support and an additive mixture solution as necessary, and dipping the membrane in a reagent such as sulfuric acid to be subjected to a sulfonation reaction. The compound represented by Formula 1 above includes a butylbenzene group to which an —$OM_1$ group is bonded in the molecule, and is applied during the preparation of a polymer electrolyte membrane such that the —$OM_1$ group of the butylbenzene group to which the —$OM_1$ group is bonded is exchanged with a —OH group by an ion exchange reaction to form a hindered phenol group (3,5-di-tert-butyl-4-hydroxyphenyl group) as an antioxidant group in the polymer electrolyte membrane, and the hindered phenol group reacts with oxygen radicals of ROS instead of the polymer electrolyte membrane by a reduction reaction of the —OH group thereof to prevent oxidation, thereby improving the chemical durability of the polymer electrolyte membrane.

In addition, since the compound represented by Formula 1 has a structure in which the —$OM_1$ group is bonded at position 1 of the benzene group and a t-butyl group, which is capable of providing a large amount of electrons, at positions 2 and 6 adjacent thereto, the —OH group (derived from the —$OM_1$ group) at the position 1 by the t-butyl group at positions 2 and 6 smoothly generates radicals such as —O— and reacts with radicals generated during the driving of the fuel cell, thereby more effectively preventing oxidation.

In addition, an additive, such as an inorganic-based antioxidant, commonly used to improve the durability of the polymer electrolyte membrane suppresses decomposition of the polymer electrolyte membrane by the ROS, thereby improving the durability, but there is a limitation that the proton conductivity is reduced by forming an ionic bond with a cation exchange group (—$SO_3$—) introduced into the polymer electrolyte membrane to block a proton exchange channel. However, the compound represented by Formula 1 above according to the present disclosure includes a perfluorinated sulfonate group (e.g., —$CF_2SO_3Na$) as an ion conductive functional group in conjunction with an —$OM_1$ group-bonded butylbenzene group forming the antioxidant functional group in the molecule, thereby improving the chemical durability of the polymer electrolyte membrane and simultaneously improving the proton conductivity.

Meanwhile, as shown in Reaction Scheme 1, which will be described below, the compound represented by Formula 1 above is synthesized by reacting a compound providing an ion conductive functional group to a hindered phenol, and a reaction may occur only at position 4 of the phenol group due to reaction activity, and thus the compound represented by Formula 1 above according to an embodiment of the present disclosure has a structure in which an —$OM_1$ group is bonded at position 1 of the benzene group, a t-butyl group is bonded at positions 2 and 6 adjacent thereto, and an ion conductive functional group is bonded at position 4.

Specifically, in Formula 1 above, $R_1$ to $R_4$ may be each independently a hydrogen atom, an alkyl group having 1 to 3 carbon atoms, a fluoro-substituted alkyl group having 1 to 3 carbon atoms, or a fluorine atom, wherein at least one among $R_1$ to $R_4$ may be a fluorine atom.

In addition, in Formula 1 above, A may be —O— or —S—.

In addition, in Formula 1 above, $M_1$ and $M_2$ may be each independently potassium or sodium.

As another example, in Formula 1 above, $R_1$ to $R_4$ may all be fluorine atoms, A may be —O—, $M_1$ and $M_2$ may be sodium, and n and m may be each independently an integer of 1 to 3.

More specifically, the compound represented by Formula 1 may be a compound represented by Formula 1-1 below:

[Formula 1-1]

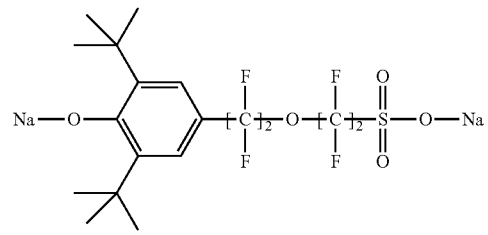

Meanwhile, the compound represented by Formula 1 above according to an embodiment of the present disclosure may be prepared by reacting a compound represented by Formula a and a compound represented by Formula b to prepare a compound represented by Formula c, which is a precursor compound, and reacting the compound represented by Formula c with an alkali metal hydroxide, as shown in Reaction Scheme 1 below:

[Reaction Scheme 1]

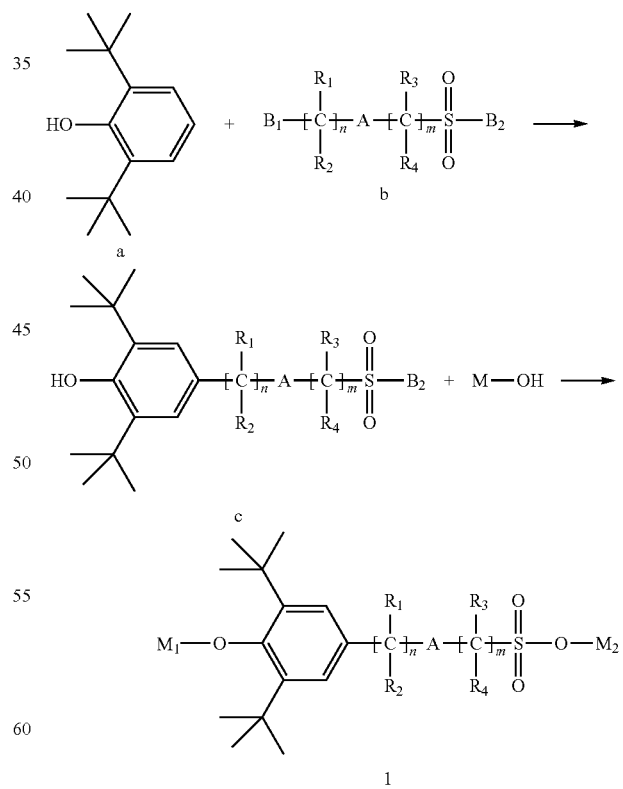

In Reaction Scheme 1 above, $R_1$ to $R_4$, A, $M_1$, $M_2$, n and m may be the same as defined in Formula 1, and $B_1$ and $B_2$ may be each independently F, Cl, Br or I. $B_1$ and $B_2$ above may be each independently F, Cl, Br or I, and may be different from each other, and more specifically, $B_1$ may be I and $B_2$ may be F.

Polymer Electrolyte Membrane

In addition, the present disclosure provides a polymer electrolyte membrane including a unit derived from the compound.

The polymer electrolyte membrane according to an embodiment of the present disclosure includes a unit derived from the compound represented by Formula 1 above, and the unit derived from the compound represented by Formula 1 above may be included as a monomer polymerized in a polymer constituting the polymer electrolyte membrane or may be included as an additive, and specifically, may be included as an additive.

Here, the unit derived from the compound represented by Formula 1 may be a compound represented by Formula 2 below:

[Formula 2]

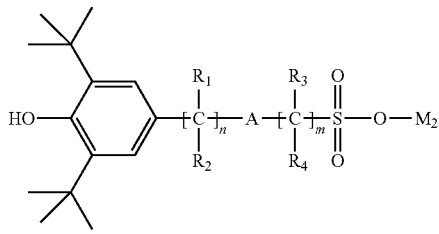

In Formula 2 above, $R_1$ to $R_4$, A, $M_2$, n and m are the same as defined in Formula 1.

The compound represented by Formula 1 according to an embodiment of the present disclosure may be present in the same structure as the compound represented by Formula 2 in the polymer electrolyte membrane because the $—OM_1$ group forms a —OH group by ion exchange during the sulfonation reaction for forming the polymer electrolyte membrane when applied to the polymer electrolyte membrane.

When the compound represented by Formula 1 above is included as an additive of the polymer electrolyte membrane, the polymer electrolyte membrane may include a polymer support and a unit derived from the compound represented by Formula 1 above, and the unit derived from the compound represented by Formula 1 above may be included in an amount of 0.5 wt % to 2.0 wt % with respect to 100 wt % of the polymer.

In addition, the polymer support is not particularly limited as long as it is commonly known, but may be, for example, at least one among a perfluorosulfonic acid polymer, a hydrocarbon-based polymer, polyimide, polyvinylidene fluoride, polyethersulfone, polyphenylene sulfide, polyphenylene oxide, polyphosphazine, polyethylene naphthalate, polyester, doped polybenzimidazole, polyetherketone, polysulfone, or an acid or a base thereof.

In addition, the polymer electrolyte membrane according to an embodiment of the present disclosure may be prepared by a material or method commonly known in the art except for including the unit derived from the compound represented by Formula 1, and may also have a thickness of several microns to several hundred microns.

Meanwhile, the polymer electrolyte membrane according to the present disclosure includes the unit derived from the compound represented by Formula 1, and thus may have excellent chemical durability, thermal stability, and mechanical properties, and also may have excellent proton conductivity.

For example, the polymer electrolyte membrane may have a proton conductivity of 24 mS/cm to 38 mS/cm under the conditions of 80° C. and 50% relative humidity (RH).

In addition, the polymer electrolyte membrane may have a proton conductivity of 92 mS/cm to 120 mS/cm under the conditions of 80° C. and 90% relative humidity (RH).

In addition, the polymer electrolyte membrane may have an ion exchange capacity (IEC) of 0.70 mEq/g to 0.80 mEq/g.

Membrane Electrode Assembly

Also, the present disclosure provides a membrane electrode assembly including the polymer electrolyte membrane.

The membrane electrode assembly according to an embodiment of the present disclosure includes: an anode; a cathode; and the polymer electrolyte membrane provided between the anode and the cathode.

As another example, the membrane electrode assembly may include the polymer electrolyte membrane and the anode and the cathode facing each other with the polymer electrolyte membrane located therebetween.

The anode may include an anode catalyst layer and an anode gas diffusion layer, and the anode gas diffusion layer may also include an anode micropore layer and an anode electrode substrate. In this case, the anode gas diffusion layer is provided between the anode catalyst layer and the polymer electrolyte membrane.

In addition, the cathode may include a cathode catalyst layer and a cathode gas diffusion layer, and the cathode gas diffusion layer may also include a cathode micropore layer and a cathode electrode substrate. In this case, the cathode gas diffusion layer is provided between the cathode catalyst layer and the polymer electrolyte membrane.

The anode catalyst layer is a place where the oxidation reaction of the fuel occurs, and a catalyst selected from the group consisting of platinum, ruthenium, osmium, a platinum-ruthenium alloy, a platinum-osmium alloy, a platinum-palladium alloy, and a platinum-transition metal alloy may be used, and the cathode catalyst layer is a place where the reduction reaction of the oxidizer occurs, and platinum or a platinum-transition metal alloy may be used as a catalyst. Here, the catalyst may be used by itself or may be used by being supported on a carbon-based carrier.

In addition, the catalyst layer of each electrode may be introduced into an electrode by a method commonly known in the art, and for example, a catalyst layer may be formed by directly coating a polymer electrolyte membrane with a catalyst ink or by coating a gas diffusion layer with a catalyst ink. In this case, the coating method of the catalyst ink is not particularly limited, but for example, spray coating, tape casting, screen printing, blade coating, die coating, or spin coating may be used. In addition, the catalyst ink may include a catalyst, a polymer ionomer, and a solvent.

The gas diffusion layer of each electrode serves as a current conductor and becomes a passage for the movement of the reaction gas and water, and may have a porous structure. Accordingly, the gas diffusion layer may include a conductive substrate, and as the conductive substrate, for example, carbon paper, carbon cloth, or carbon felt may be used. In addition, the gas diffusion layer may further include a micropore layer between the catalyst layer and the electrode substrate, and the micropore layer may serve to reduce an amount of water flowing out of the gas diffusion layer to maintain a sufficient wet state of the polymer electrolyte membrane, thereby improving the performance of the fuel cell under low-humidity conditions.

Fuel Cell

Furthermore, the present disclosure provides a fuel cell including the membrane electrode assembly.

The fuel cell according to an embodiment of the present disclosure includes: a stack including the at least two membrane electrode assemblies and a separator provided between the membrane electrode assemblies; a fuel supplier configured to supply fuel to the stack; and an oxidizer supplier configured to supply an oxidizer to the stack.

The stack may include the at least two membrane electrode assemblies, and may be provided with the separator between the membrane electrode assemblies. The separator may serve to prevent the membrane electrode assemblies from being electrically connected, and transfer the fuel and oxidizer supplied from the outside to the membrane electrode assemblies.

The oxidizer supplier serves to supply the oxidizer to the stack, and oxygen may be typically used as the oxidizer, and oxygen or air may be injected with a pump.

In addition, the fuel supplier serves to supply the fuel to the stack, and may include a fuel tank configured to store the fuel and a pump configured to supply the fuel stored in the fuel tank to the stack. In addition, as the fuel, hydrogen or hydrocarbon in a gaseous or liquid state may be used, and the hydrocarbon may include methanol, ethanol, propanol, butanol, or natural gas.

EXAMPLES

Hereinafter, the present disclosure will be described in more detail according to examples. However, the example according to the present disclosure may be modified in many different forms, and the scope of the present disclosure should not be interpreted to be limited to the examples described below. Rather, the example of the present disclosure is provided so that this description will be thorough and complete, and will fully convey the scope of the present disclosure to those skilled in the art.

Example 1

(1) Preparation of 2-(2-(3,5-di-tert-butyl-4-hydroxyphenyl)-1,1,2,2-tetrafluoroethoxy)-1,1,2,2-tetrafluoroethanesulfonyl fluoride 2,6-di-tert-butylphenol (0.2 g, 0.96 mmol) and tetrafluoro-2-(tetrafluoro-2-iodoethoxy) ethanesulfonyl fluoride (2.47 g, 6.0 mmol) were stirred and reacted at 70° C. for 48 hours in 4 mL of a solvent ($CHCl_3$:$H_2O$=1:1) using a catalyst composed of $Na_2S_2O_4$ (1.7 g, 9.6 mmol), $NaHCO_3$ (0.07 g, 0.84 mmol), and hexadecyltrimethylammonium bromide (0.35 g, 0.96 mmol). After the reaction, 1M HCl (0.8 mL) was added to adjust the pH to 1-2, the mixture was diluted with 2 mL of distilled water, and extracted using diethylether (3×10 mL) and brine (2×10 mL), and purified by column chromatography (100% hexane) to prepare 2-(2-(3,5-di-tert-butyl-4-hydroxyphenyl)-1,1,2,2-tetrafluoroethoxy)-1,1,2,2-tetrafluoroethanesulfonyl fluoride, which is a precursor compound, and the synthesis was confirmed through $^1H$ NMR ($CDCl_3$) and $^{19}F$ NMR ($CDCl_3$) analyses, and the results are shown in FIG. 1.

As shown in FIG. 1, a phenyl ring peak (peak 1), a methyl group partial peak (peak 2), and a —OH peak (peak 3) of the phenol group were identified in the 1H NMR result. In addition, —$CF_2$ peaks (peaks 1, 2, 3, and 4) and a sulfonyl fluoride peak (peak 5) were identified from the results of 19F NMR.

Figure 2:
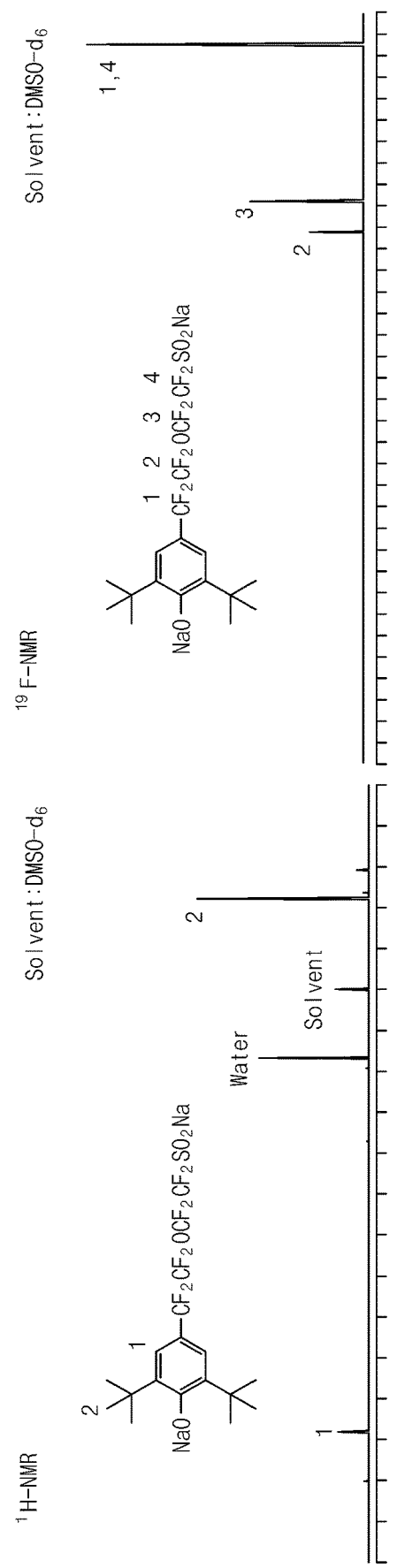
FIG. 2 shows the results of $^1$H NMR and $^{19}$F NMR of a compound prepared in Example 1 according to an embodiment of the present disclosure.

(2) Preparation of sodium 2-(2-(3,5-di-tert-butyl-4-oxidophenyl)-1,1,2,2-tetrafluoroethoxy)-1,1,2,2-tetrafluoroethanesulfonate 2-(2-(3,5-di-tert-butyl-4-hydroxyphenyl)-1,1,2,2-tetrafluoroethoxy)-1,1,2,2-tetrafluoroethanesulfonyl fluoride (1 g, 1.98 mmol) and NaOH (0.23 g, 5.95 mmol) prepared in 3 mL of distilled water were reacted at 95° C. for 16 hours. Then, the solvent was removed using an evaporator, the organic layer was dissolved by adding ethanol and then vacuum-filtered to remove the salt, and dried in a 50° C.-vacuum oven for 12 hours to prepare sodium 2-(2-(3,5-di-tert-butyl-4-oxidophenyl)-1,1,2,2-tetrafluoroethoxy)-1,1,2,2-tetrafluoroethanesulfonate, which is a compound represented by Formula 1-1, and the synthesis was confirmed through $^1H$ NMR (DMSO-$d_6$) and $^{19}F$ NMR (DMSO-$d_6$) analyses, and the results are shown in FIG. 2. In addition, the synthesis of the compound was confirmed through FT-IR analysis, and the result is shown in FIG. 3.

As shown in FIG. 2, in the 1H NMR result, it was confirmed that the phenyl ring peak (peak 1) was shifted and changed, and the —OH peak (peak 3) of the phenol group disappeared as compared with FIG. 1. In addition, in the $^{19}F$ NMR result, it was confirmed that the —$CF_2$ peaks (peaks 1, 2, 3, and 4) were slightly shifted and the sulfonyl fluoride peak (peak 5) disappeared as compared with FIG. 1.

Figure 3:
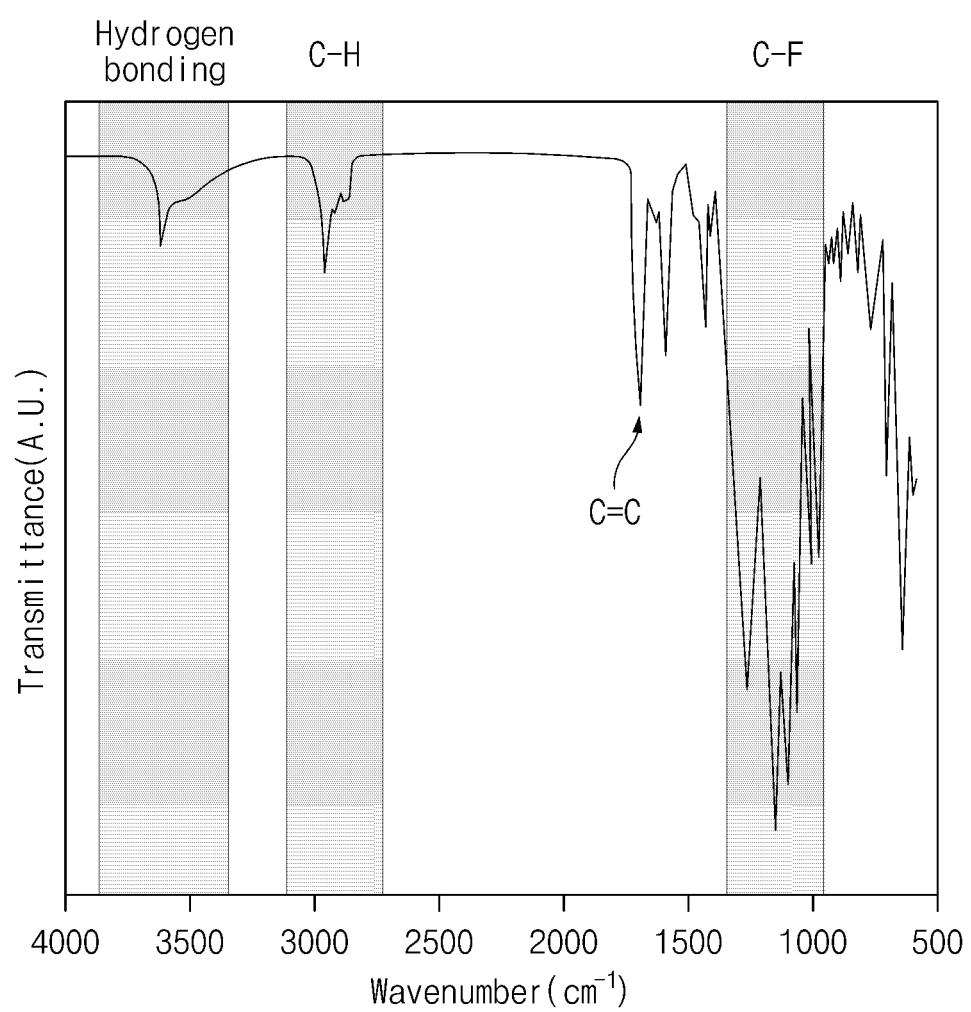
FIG. 3 shows the FT-IR result of the compound prepared in Example 1 according to an embodiment of the present disclosure.

As shown in FIG. 3, a hydrogen bond peak may be identified around 3615 $cm^{-1}$, and thus it was confirmed that the peak of —OH of the phenol group is substituted with —O—$Na^+$, and a C—H peak was identified around 2960 $cm^{-1}$, and a C—F bond around 1200 $cm^{-1}$.

Experimental Example 1

Thermal stability and solubility of the compound of Example 1 were compared and analyzed.

(1) Thermal Stability

The thermal stability was confirmed through thermogravimetric analysis (TGA), and specifically, each compound sample was put into a heating furnace of the thermogravimetric analyzer, and the temperature was elevated from room temperature to 120° C. at 20° C./min and maintained for 10 minutes, thereby removing the remaining water and performing stabilization. Thereafter, the weight change of the sample was measured while cooling to 60° C. at 20° C./min and heating from 60° C. to 800° C. at 10° C./min in a nitrogen atmosphere, and the results are shown in Table 1 below.

(2) Solubility

Figure 4:
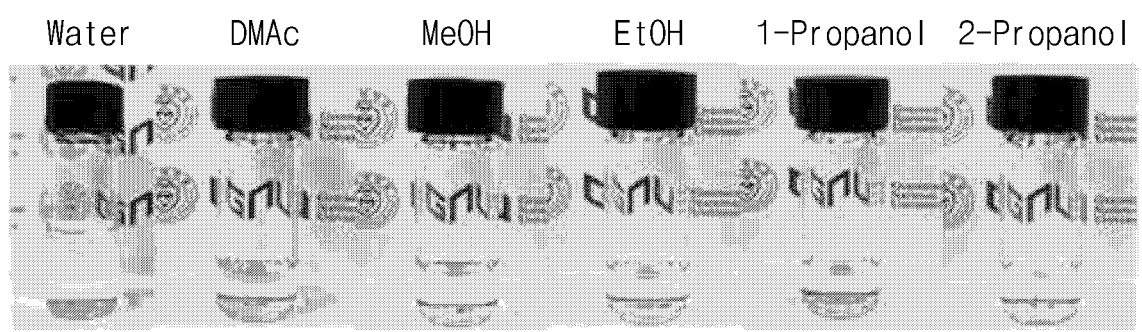
FIG. 4 shows the result in which solubility of the compound prepared in Example 1 according to an embodiment of the present disclosure is observed with the naked eye.

The solubility of each compound sample was observed by dissolving the same amount in a total of six solvents, including water, dimethylacetamide (DMAc), methanol, ethanol, 1-propanol and 2-propanol, and the results are shown in Table 1 and FIG. 4. In the results, if the phase separation is not visible with the naked eye and the sample is dissolved well, it is indicated as ○, and if the phase separation is visible or the sample is not dissolved, it is indicated as x.

TABLE 1

| Division | Thermal stability 5% decomposition temperature | Solubility | | | | | |
|---|---|---|---|---|---|---|---|
| | | Water | DMAc | Methanol | Ethanol | 1-propanol | 2-propanol |
| Example 1 | 255° C. | x | ○ | ○ | ○ | ○ | ○ |

Referring to Table 1 above, it was confirmed that the compound of Example 1 is not dissolved in water and the decomposition occurs when the temperature reaches a very high temperature.

Example 2

A polymer electrolyte membrane including the compound prepared in Example 1 as an additive was prepared.

0.5 wt % of the compound prepared in Example 1 with respect to Nafion was added to 3 g of 20 wt % Nafion solution, stirred at room temperature for 1 hour to prepare a solution, and the solution was cast on a glass plate and dried in a 60° C.-oven for 3 hours to prepare a membrane. Thereafter, the membrane was separated from the glass plate using a moisture penetration method, impregnated with 1 M sulfuric acid solution at 60° C. for 6 hours, and then washed until neutral. Then, the membrane was dried at 50° C. for 2 hours using a gel dryer to prepare a polymer electrolyte membrane having a thickness of 50 μm.

Example 3

A polymer electrolyte membrane was prepared in the same manner as in Example 2, except that the compound prepared in Example 1 was added in an amount of 1.0 wt % with respect to the Nation.

Example 4

A polymer electrolyte membrane was prepared in the same manner as in Example 2, except that the compound prepared in Example 1 was added in an amount of 2.0 wt % with respect to the Nation.

Comparative Example

A polymer electrolyte membrane was prepared in the same manner as in Example 2, except that the compound prepared in Example 1 was not added.

Experimental Example 2

The thermal stability, chemical durability, mechanical properties, ion exchange capacity, and proton conductivity of each of the polymer electrolyte membranes prepared in Examples 2 to 4 and Comparative Example were compared and analyzed.

(1) Thermal Stability

Figure 5:
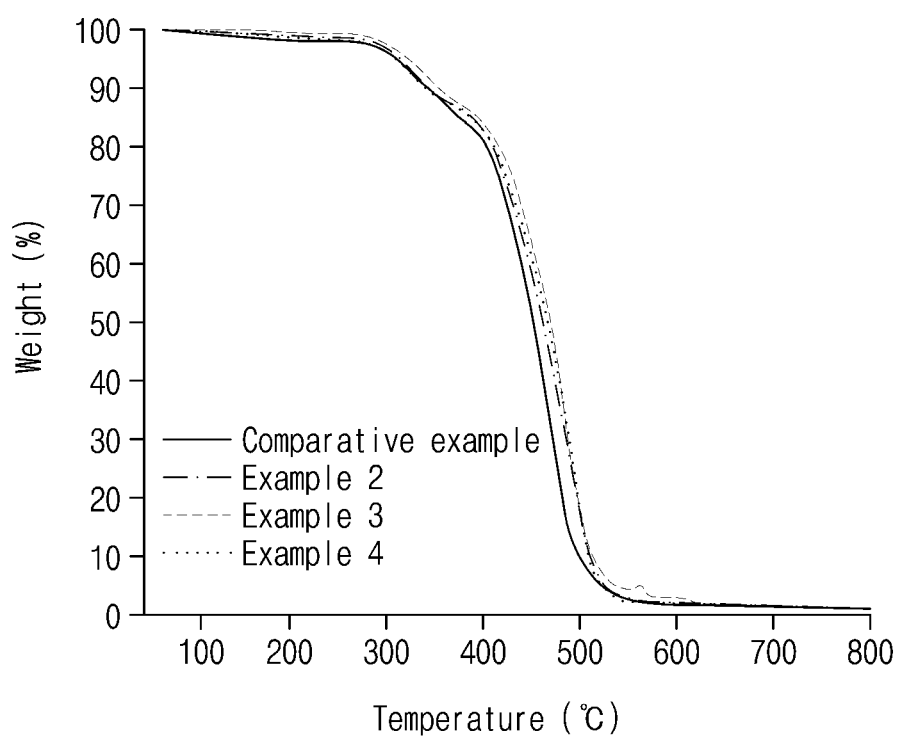
FIG. 5 shows thermogravimetric analysis results of polymer electrolyte membranes according to embodiments of the present disclosure.
Figure 6:
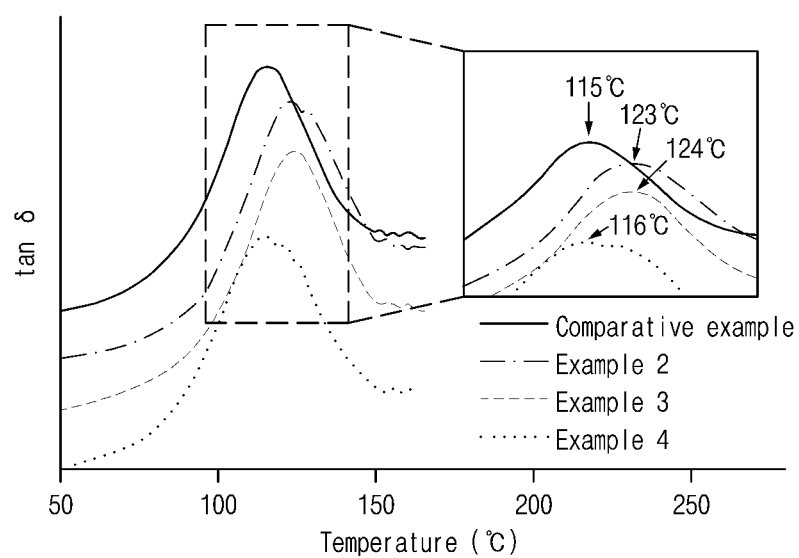
FIG. 6 shows glass transition temperature measurement results of the polymer electrolyte membranes according to embodiments of the present disclosure.

The thermal stability was confirmed through thermogravimetric analysis (TGA) and glass transition temperature (Tg) measurement, and the results are shown in Table 2, FIG. 5, and FIG. 6.

In the thermogravimetric analysis, each polymer electrolyte membrane sample was put into a heating furnace of the thermogravimetric analyzer, and the temperature was elevated from room temperature to 120° C. at 20° C./min and maintained for 10 minutes, thereby removing the remaining water and performing stabilization. Thereafter, the weight change of the sample was measured while cooling to 60° C. at 20° C./min and heating from 60° C. to 800° C. at 10° C./min in a nitrogen atmosphere.

The glass transition temperature was analyzed through a dynamic mechanical analyzer, and each polymer electrolyte membrane was cut into a size of 20 mm×5 mm and used as a sample, and the conditions were set as the frequency of 1 Hz and the amplitude of 15 μm, tan δ was measured while raising the temperature from 30° C. to 120° C. at 3° C./min, and the maximum point of tan δ was recorded as the glass transition temperature.

TABLE 2

| | Division | Examples | | | Comparative Example |
|---|---|---|---|---|---|
| | | 2 | 3 | 4 | |
| TGA | 5% decomposition temperature (° C.) | 311 | 318 | 306 | 310 |
| | Tg (° C.) | 123 | 124 | 116 | 115 |

From the results of Table 2, FIG. 5, and FIG. 6, it was confirmed that the polymer electrolyte membranes of Examples 2 to 4 including the compound of Example 1 as an additive have higher glass transition temperature and decomposition temperature than the polymer electrolyte membrane of Comparative Example, and thus it may be confirmed that the polymer electrolyte membranes of Examples 2 to 4 have excellent thermal stability.

(2) Chemical Durability

The chemical durability of the polymer electrolyte membrane was confirmed through water uptake and dimensional change. Three measurements were performed per sample, the measurement results are shown as an average value, and the results are shown in Table 3 and FIG. 7.

Each polymer electrolyte membrane dried through a desiccator was cut into a size of 1 cm×3 cm, and the thickness and weight thereof were measured. Thereafter, the cut polymer electrolyte membrane was put into a vial, filled with distilled water, stored in a 30° C.-drying oven for 12 hours, and the swollen polymer electrolyte membrane was taken out, and the area, thickness, and weight thereof were measured to confirm the water uptake and dimensional change through Equations 1 and 2 below.

$$\text{Water uptake (\%)}=[(W_{wet}-W_{dry})/W_{dry}]\times 100 \quad \text{[Equation 1]}$$

$$\text{Dimensional change (\%)}=[(A_{wet}\times T_{wet})-(A_{dry}\times T_{dry})/(A_{dry}\times T_{dry})]\times 100 \quad \text{[Equation 2]}$$

In Equations 1 and 2, $W_{dry}$ and $W_{wet}$ respectively represent the weights of the dried polymer electrolyte membrane and the swollen polymer electrolyte membrane, $A_{dry}$ and $A_{wet}$ respectively represent the areas of the dried polymer electrolyte membrane and the swollen polymer electrolyte membrane, and $T_{dry}$ and $T_{wet}$ respectively represent the thicknesses of the dried polymer electrolyte membrane and the swollen polymer electrolyte membrane.

TABLE 3

| Division | Examples | | | Comparative Example |
|---|---|---|---|---|
| | 2 | 3 | 4 | |
| Water uptake (%) | 23.02 | 22.02 | 25.29 | 30.88 |
| Dimensional change (%) | 31.21 | 28.05 | 35.97 | 47.48 |

Figure 7:
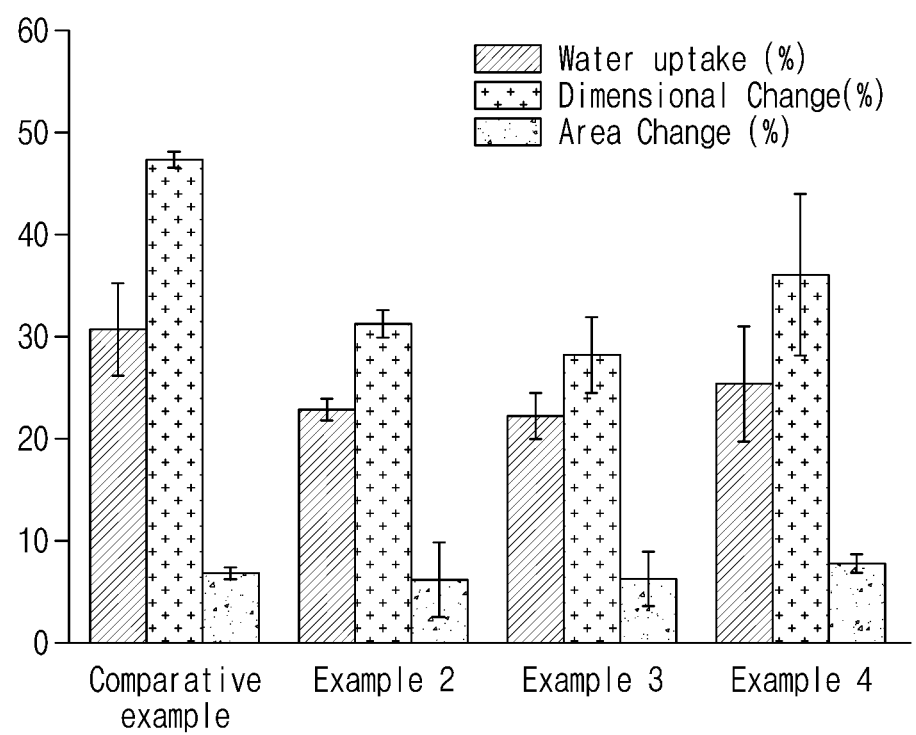
FIG. 7 is a graph showing the measurement results of water uptake and dimensional change of the polymer electrolyte membranes according to embodiments of the present disclosure.

Referring to Table 3 and FIG. 7, it may be confirmed that the polymer electrolyte membranes of Examples 2 to 4 have significantly less water absorption and dimensional change than the polymer electrolyte membrane of Comparative Example, and thus it may be confirmed that the polymer electrolyte membranes of Examples 2 to 4 have excellent chemical durability.

(3) Mechanical Properties

The mechanical properties of each polymer electrolyte membrane were confirmed through tensile strength, elastic modulus, and elongation.

Specifically, 250 N of Load cell was coupled to the LLOYD UTM LS1 device, each polymer electrolyte membrane specimen prepared according to ASTM D638 type V was engaged, and then tensile strength, elastic modulus, and elongation thereof were measured at an extension rate of 5 mm/min. In this case, each specimen was measured seven times, the measurement results were shown as an average value thereof, and the results are shown in Table 4 below:

TABLE 4

| Division | Examples | | | Comparative Example |
|---|---|---|---|---|
| | 2 | 3 | 4 | |
| Tensile strength (MPa) | 12.23 | 11.25 | 12.17 | 11.93 |
| Elastic modulus (MPa) | 268.21 | 341.58 | 297.51 | 250.38 |
| Elongation (%) | 53.90 | 52.30 | 41.20 | 31.97 |

Referring to Table 4, it was confirmed that the polymer electrolyte membranes of Examples 2 to 4 have mechanical properties remarkably superior to the polymer electrolyte membrane of Comparative Example.

(4) Proton Conductivity

The proton conductivity was measured in two states: a state in which oxidation was not induced and a state in which oxidation was induced.

1) Uninduced Oxidation Proton Conductivity

The proton conductivity was measured by cutting each polymer electrolyte membrane into a specimen having a size of 0.5 cm×3 cm, engaging the specimen with a four-probe cell, maintaining a temperature/humidity equilibrium for 2 hours under conditions of 80° C. and 70% relative humidity (RH) before measurement, and measuring the proton conductivity by dropping the humidity from 70% RH to 20% RH, and then measuring the proton conductivity by increasing the humidity from 20% RH to 100% RH by using BekkTech BT-552MX equipment. Each polymer electrolyte membrane was measured three times, and the results are shown in Table 5 and FIG. 8 as an average value thereof.

TABLE 5

| Division | | Examples | | | Comparative Example |
|---|---|---|---|---|---|
| | | 2 | 3 | 4 | |
| Proton conductivity (mS/cm) | 30% RH | 10.2 | 11.6 | 10.5 | 9.6 |
| | 50% RH | 27.7 | 33.3 | 29.0 | 26.4 |
| | 70% RH | 55.8 | 63.6 | 56.6 | 50.8 |
| | 90% RH | 100.4 | 109.1 | 99.8 | 87.2 |

Figure 8:
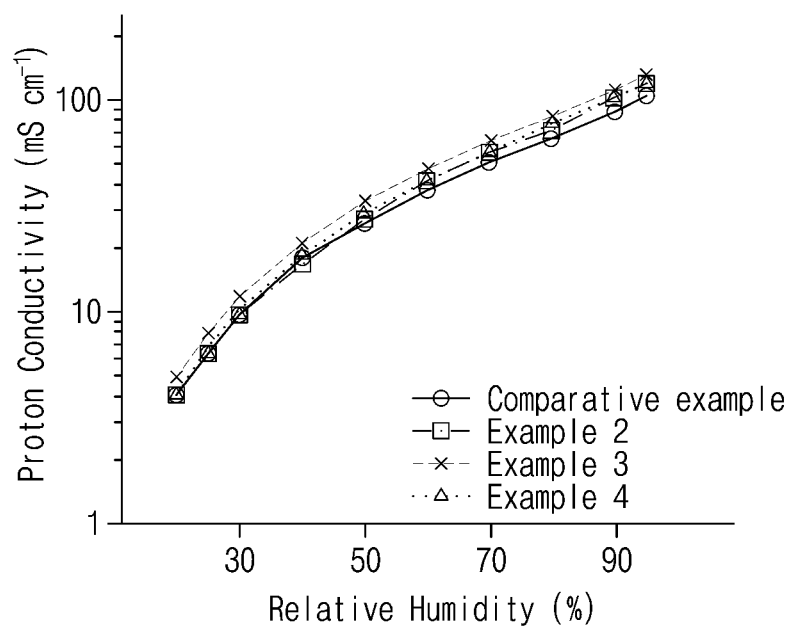
FIG. 8 shows proton conductivity measurement results of the polymer electrolyte membranes according to embodiments of the present disclosure.

Referring to Table 5 and FIG. 8, it was confirmed that the polymer electrolyte membranes of Examples 2 to 4 have significantly improved proton conductivity as compared with the polymer electrolyte membrane of Comparative Example.

2) Proton Conductivity after Oxidation Induction (Fenton's Test)

Each of the polymer electrolyte membranes of Example 3 and Comparative Example 2 was cut into a specimen having a size of 0.5 cm×3 cm, the weight thereof was measured, and then put into a 30 mL-vial, and then, 25 mL of Fenton's reagent (3 wt % hydrogen peroxide, 4 ppm iron sulfate aqueous solution) was added into the vial, and the specimen was impregnated with the reagent at 80° C. for 24 hours. Thereafter, each specimen, which has been impregnated, was washed several times with distilled water and dried, and then the proton conductivity was measured in the same manner as in the method of 1) above. The results are shown in Table 6 below:

TABLE 6

| Division | | Example 2 | | Comparative Example | |
|---|---|---|---|---|---|
| | | Before oxidation induction | After oxidation induction | Before oxidation induction | After oxidation induction |
| Proton conductivity (mS/cm) | 50% RH | 26.1 | 27.4 | 25.0 | 21.9 |
| | 70% RH | 60.3 | 59.2 | 53.4 | 48.2 |
| | 90% RH | 99.1 | 107.8 | 92.1 | 89.3 |

Referring to Table 6, in the case of Example 2, the proton conductivity was not significantly changed before and after the oxidation induction, and the proton conductivity was superior to that of the Comparative Example, but in the case of the Comparative Example, the proton conductivity after oxidation was significantly decreased as compared with that before oxidation. This means that the polymer electrolyte membrane of Example 2 is prevented from being oxidized, and thus the compound of the present disclosure has excellent antioxidant effects.

(5) Ion Exchange Capacity

Each dried polymer electrolyte membrane was weighed, and then put into a 30 mL-vial, 15 mL of 1M NaCl solution was added to the vial, and then stirred at 60° C. for 6 hours or more to prepare a specimen for measuring the ion exchange capacity. A 0.01 M NaOH solution was added to the vial containing the polymer electrolyte membrane using a potentiometric titrator (TITRANDO 888) until the pH of the vial internal solution reached 7.0 to check the total input NaOH volume, and then the ion exchange capacity was calculated with Equation 3 below, and the results are shown in Table 7 below.

$$IEC_w = [C_{NaOH} \times (\Delta V_{NaOH}/W_s)] \times 1000 \quad \text{[Equation 3]}$$

In Equation 3, $C_{NaOH}$ represents the concentration of NaOH (0.01 M), $\Delta V_{NaOH}$ represents the total volume of the injected NaOH, and $W_s$ represents the weight of the dried polymer electrolyte membrane.

TABLE 7

| Division | Examples | | | Comparative Example |
|---|---|---|---|---|
| | 2 | 3 | 4 | |
| Ion exchange capacity (mEq/g) | 0.74 | 0.75 | 0.75 | 0.74 |

Referring to Table 7, it was confirmed that the polymer electrolyte membranes of Examples 2 to 4 exhibited excellent ion exchange capacity equal to or higher than that of the Comparative Example.

From the results shown in Tables 2 to 7 and FIGS. 4 to 8, it was confirmed that the compound represented by Formula 1 according to an embodiment of the present disclosure has excellent antioxidant and ion conducting effects, and also the polymer electrolyte membrane of the present disclosure includes the compound as an additive, thereby having excellent chemical durability, thermal stability, and mechanical stability and significantly improving the proton conductivity.

The compound according to the present disclosure includes both an antioxidant functional group and an ion conductive functional group in the molecule, and thus is applied as an additive for the polymer electrolyte membrane, thereby improving the chemical durability, thermal stability, and mechanical stability of the polymer electrolyte membrane and simultaneously improving performance such as proton conductivity.

The polymer electrolyte membrane according to the present disclosure includes the compound represented by Formula 1 as an additive, and thus has improved chemical durability, thermal stability, and mechanical stability, and also has excellent performance such as proton conductivity.

The membrane electrode assembly and the fuel cell according to the present disclosure are provided with the polymer electrolyte membrane, and thus have excellent durability and efficiency.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A compound represented by Formula 1 below:

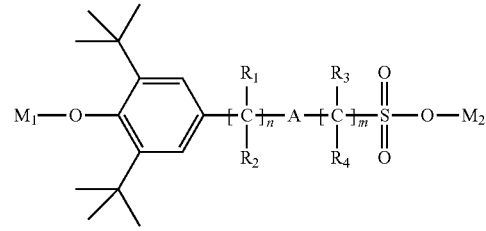

wherein $R_1$ to $R_4$ are each independently a hydrogen atom, an alkyl group having 1 to 6 carbon atoms, a fluoro-substituted alkyl group having 1 to 6 carbon atoms, or a fluorine atom, wherein at least one among $R_1$ to $R_4$ is a fluorine atom, A is a divalent linking group, $M_1$ and $M_2$ are each independently potassium or sodium, and n and m are each independently an integer of 1 to 10.

2. The compound of claim 1, wherein $R_1$ to $R_4$ are each independently the hydrogen atom, where at least one among $R_1$ to $R_4$ is the fluorine atom.

3. The compound of claim 1, wherein the alkyl group has 1 to 3 carbon atoms, where at least one among $R_1$ to $R_4$ is the fluorine atom.

4. The compound of claim 1, wherein the fluoro-substituted alkyl group has 1 to 3 carbon atoms, where at least one among $R_1$ to $R_4$ is the fluorine atom.

5. The compound of claim 1, wherein $R_1$ to $R_4$ are the fluorine atom.

6. The compound of claim 1, wherein, A is —O— or —S—.

7. The compound of claim 1, wherein, $M_1$ and $M_2$ are potassium.

8. The compound of claim 1, wherein, $M_1$ and $M_2$ are sodium.

9. The compound of claim 1, wherein $R_1$ to $R_4$ are the fluorine atom,

A is —O—, $M_1$ and $M_2$ are sodium, and n and m are each independently an integer of 1 to 3.

10. The compound of claim 1, wherein the compound represented by Formula 1 is represented by Formula 1-1 below:

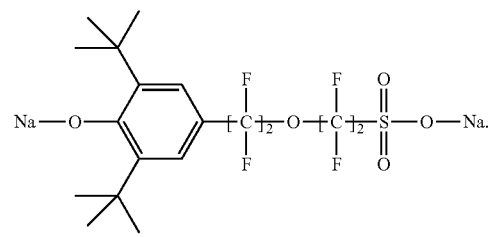

11. A polymer electrolyte membrane comprising the compound of claim 1.

12. The polymer electrolyte membrane of claim 11, wherein the polymer electrolyte membrane has a proton conductivity of 24 mS/cm to 38 mS/cm under the conditions of 80° C. and 50% relative humidity (RH).

13. The polymer electrolyte membrane of claim 11, wherein the polymer electrolyte membrane has a proton conductivity of 92 mS/cm to 120 mS/cm under the conditions of 80° C. and 90% relative humidity (RH).

14. The polymer electrolyte membrane of claim 11, further comprising a polymer support, and the compound is comprised in an amount of 0.5 wt % to 2.0 wt % based on a weight of the polymer support.

15. A fuel cell comprising:
- a stack comprising at least two membrane electrode assemblies and a separator disposed between the membrane electrode assemblies;
- a fuel supplier configured to supply fuel to the stack; and
- an oxidizer supplier configured to supply an oxidizer to the stack,
- wherein the membrane electrode assembly comprising an anode; a cathode; and the polymer electrolyte membrane of claim 11 disposed between the anode and the cathode.

* * * * *